US012773392B2

(12) United States Patent
Linn et al.

(10) Patent No.: US 12,773,392 B2
(45) Date of Patent: Oct. 27, 2026

(54) ORAL THIN FILM COMPRISING A PVA-TRIS BUFFER LAYER

(71) Applicant: LTS LOHMANN THERAPIE-SYSTEME AG, Andernach (DE)

(72) Inventors: Michael Linn, Waldböckelheim (DE); Mario Ficker, Bonn (DE); Claudia Norelli, Hillscheid (DE); Markus Müller, Troisdorf (DE); Christoph Schmitz, Rheinbrohl (DE)

(73) Assignee: LTS LOHMANN THERAPIE-SYSTEME AG, Andernach (DE)

( * ) Notice: Subject to any disclaimer, the term of this patent is extended or adjusted under 35 U.S.C. 154(b) by 483 days.

(21) Appl. No.: 18/272,226

(22) PCT Filed: Jan. 14, 2022

(86) PCT No.: PCT/EP2022/050794
§ 371 (c)(1),
(2) Date: Jul. 13, 2023

(87) PCT Pub. No.: WO2022/152878
PCT Pub. Date: Jul. 21, 2022

(65) Prior Publication Data

US 2024/0165052 A1 May 23, 2024

(30) Foreign Application Priority Data

Jan. 15, 2021 (DE) ........................ 102021100780.1

(51) Int. Cl.
*A61K 31/135* (2006.01)
*A61K 9/00* (2006.01)
*A61K 9/70* (2006.01)
*A61K 47/18* (2017.01)
*A61K 47/32* (2006.01)

(52) U.S. Cl.
CPC ............ *A61K 31/135* (2013.01); *A61K 9/006* (2013.01); *A61K 9/7007* (2013.01); *A61K 47/18* (2013.01); *A61K 47/32* (2013.01)

(58) Field of Classification Search
CPC ..... A61K 31/135; A61K 9/006; A61K 9/7007
See application file for complete search history.

(56) References Cited

FOREIGN PATENT DOCUMENTS

| | | | |
|---|---|---|---|
| DE | 102006027791 | A1 | 12/2007 |
| DE | 60129849 | T2 | 4/2008 |
| EA | 031156 | B1 | 11/2018 |
| JP | 2011516166 | A | 5/2011 |
| RU | 2705963 | C2 | 11/2019 |
| WO | 2009124096 | A1 | 10/2009 |

(Continued)

OTHER PUBLICATIONS

Chen, Xunjun, et. al.; Preparation and Physicochemical Properties of Blend Films of Feather Keratin and Poly(vinyl alcohol) Compatibilized by Tris(hydroxymethyl)aminomethane; MDPI; Polymers; Sep. 20, 2018; v. 10; 13 pages.

(Continued)

*Primary Examiner* — San Ming R Hui
(74) *Attorney, Agent, or Firm* — Lippes Mathias LLP

(57) ABSTRACT

The present invention relates to an oral thin film, comprising at least one layer which contains at least one polyvinyl alcohol and tris(hydroxymethyl)aminomethane, and to the use of such an oral thin film as a medicament.

20 Claims, 3 Drawing Sheets

(56) References Cited

FOREIGN PATENT DOCUMENTS

| | | | |
|---|---|---|---|
| WO | 2012/083269 | A1 | 6/2012 |
| WO | 2016/061026 | A1 | 4/2016 |
| WO | 2017214187 | A1 | 12/2017 |

OTHER PUBLICATIONS

Kondratyeva T.S. et al. Technologie der Darreichungsformen: Lehrbuch in 2 Bänden. Band 1.—Moskau: Medizin [Technology of dosage forms: Textbook in 2 volumes. vol. 1.—Moscow: Medicine], 1991.—496 pages, p. 36-38.
Search Report for Russian Patent Application No. 2023120914, dated Jan. 17, 2024, 2 pages.
Examination Report for Russian Patent Application No. 2023120914, dated Jan. 18, 2024, 11 pages.
Office Action for Japanese Patent Application No. 2023-548778, dated Nov. 5, 2024, 8 pages.
International Search Report for PCT/EP2022/050794, dated May 18, 2022, 4 pages.
International Preliminary Report on Patentability, mailed Jul. 20, 2023, 5 pages.

ORAL THIN FILM COMPRISING A PVA-TRIS BUFFER LAYER

The present invention relates to an oral thin film (also known by the abbreviation OTF), comprising at least one layer which contains at least one polyvinyl alcohol and tris(hydroxymethyl)aminomethane, and to the use of such an oral thin film as a medicament.

Polyvinyl alcohol (PVA) is known and widely used as a matrix polymer in oral thin films, since PVA is well suited as a matrix polymer for foam formulations or other film-like OTF formulations. However, PVA can only be processed well in solutions of low ionic strength. At high salt concentrations, for example high buffer concentrations, the PVA easily precipitates or clumps. A uniform coating appearance is then no longer possible. For many applications, such as the pH adjustment of oral saliva to an optimal pH value for active agent permeation and oral hygiene, etc., the use of stronger buffers, that is to say a higher buffer concentration, is necessary to adjust a certain pH value in the saliva or to keep it at a certain pH value, as is advantageous, for example, for constant active agent absorption.

The aim of the present invention is to overcome aforementioned disadvantages of the prior art. Especially, it is the aim of the present invention to provide an oral thin film which comprises PVA and which contains the highest possible amount of at least one buffer substance, although at the same time the formulation should be easy to process and it should be ensured that the PVA does not precipitate and/or clump. At the same time, it is desired to find a formulation which can be foamed well and which can form a film of the highest possible optical homogeneity. Furthermore, the oral thin film should allow the pH value in the patient's saliva to be adjusted over as wide a range as possible whilst also being as stable as possible. For this purpose, it should be possible to incorporate as much buffer substance as possible into the PVA.

In addition, the oral thin film should be as easy to produce as possible and should also allow multi-layer oral thin films to be constructed as simply as possible.

The above aim is addressed by a multi-layer oral thin film according to claim 1, especially by an oral thin film comprising at least one layer containing at least one polyvinyl alcohol and tris(hydroxymethyl)aminomethane (TRIS).

Figure 1:
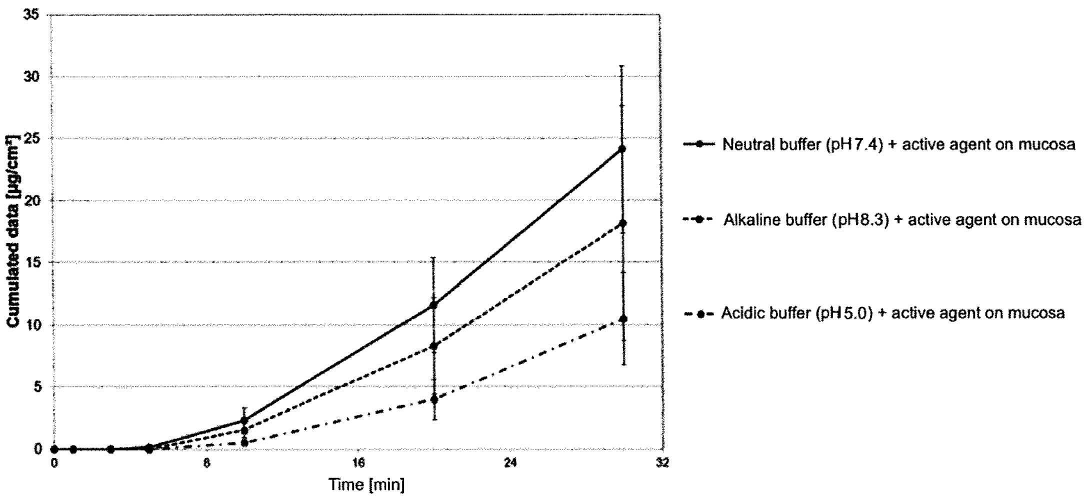
FIG. 1 shows the permeated amoount of S-ketamine in the receptor medium as measured at a temperature of 37±1 °C from Example 1.

An oral thin film comprising at least one layer which contains at least one polyvinyl alcohol and tris(hydroxymethyl)aminomethane (TRIS) will also be referred to hereinafter as a TRIS-PVA layer or a TRIS buffer layer.

Such an oral thin film has the advantage that TRIS can be incorporated in percentage and molar terms with the highest proportion of buffer/PVA. With other salts/buffers (phosphates, carbonates, citric acid, etc.), on the other hand, PVA clumps or precipitates.

The TRIS-PVA compositions can be foamed well and form a film of high optical homogeneity.

Layers with very high TRIS loading can also be produced, preferably with up to 50 wt. % TRIS. In addition, a wider pH range can be covered by adjusting with acid (for example HCl). Another advantage is that, in some embodiments, these oral thin films can be laminated together without further adhesive, i.e. it is possible to produce relatively thick multi-layer films by laminating together multiple layers of TRIS-PVA layers. The TRIS buffer layers can be co-administered with active-agent-containing OTFs to maintain a suitable pH in the oral cavity. This can be done either by sequentially administering a TRIS buffer layer and an active agent OTF (or vice versa), or the TRIS buffer layer is combined with an active agent layer (for example lamination to form multi-layer OTFs), or the TRIS buffer layer itself contains at least one pharmaceutically active agent. Especially with ketamine as the pharmaceutically active agent, systems could be created for example which are advantageous for clinical reproducibility (compensates for fluctuations in the mouth/saliva pH value) and buffers the oral cavity to an advantageous pH for permeation.

As used herein, "comprising" may also mean "consisting of".

TRIS is an abbreviation for tris(hydroxymethyl)aminomethane (THAM), also called tromethamine, trometamol (INN) as well as TRIS buffer. Chemically, it is a primary amine with three alcoholic hydroxy groups.

TRIS is used as a buffer substance for biochemical, molecular biological, microbiological and pharmaceutical purposes. With a pKs of 8.2 (at 20 °C), TRIS has a good buffering capacity between pH 7.2 to 9.0.

Polyvinyl alcohols (abbreviated PVA or PVAL, occasionally also PVOH) are polymers of the general structure

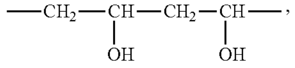

which in small proportions (about 2%) can also contain structural units of the type

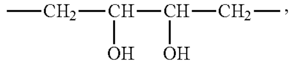

They belong to the group of vinyl polymers.

Commercially available polyvinyl alcohols, which are offered as white-yellowish powders or granular materials with degrees of polymerisation in the range of from about 500 to 2,500 (molar masses of about 20,000 to 100,000 g/mol), usually have degrees of hydrolysis of from 98 to 99 or 87 to 89 mol %, i.e. they still contain a residual content of acetyl groups. The polyvinyl alcohols are characterised by the manufacturers by specification of the degree of polymerisation of the starting polymer, the degree of hydrolysis, the saponification number and/or the solution viscosity.

According to the present invention, polyvinyl alcohols having a mean molecular weight of about 31,000 (4-88) to about 205,000 (40-88) g/mol are especially suitable.

Furthermore, according to the present invention, polyvinyl alcohols with a viscosity of from 3.4-4.6 mPas (4-88) to 34-46 mPas (40-88) mPas in a 40 g/l aqueous solution, determined by the falling ball method (Ph.Eur. 2.2.49), are especially suitable, or mixtures of two or more different PVA types.

The oral thin film according to the invention is preferably characterised in that polyvinyl alcohol is contained in the at least one layer in an amount of from 20 to 90 wt. %, preferably from 40 to 80 wt. %, and very especially preferably from 50 to 75 wt. %, in relation to the total weight of the at least one layer.

The oral thin film according to the invention is additionally preferably characterised in that polyvinyl alcohol is contained in the at least one layer in an amount of from 20 to 50 wt. %, preferably from 25 to 45 wt. %, and very especially preferably from 30 to 40 wt. %, in relation to the total weight of the at least one layer.

The oral thin film according to the invention is additionally preferably characterised in that polyvinyl alcohol is contained in the at least one layer in an amount of from 60 to 85 wt. %, preferably from 65 to 80 wt. %, and very especially preferably from 65 to 75 wt. %, in relation to the total weight of the at least one layer.

The oral thin film according to the invention is further preferably characterised in that tris(hydroxymethyl)aminomethane is contained in the at least one layer in an amount of from 3 to 70 wt. %, preferably from 10 to 55 wt. %, and very especially preferably from 15 to 50 wt. %, in relation to the total weight of the at least one layer.

The oral thin film according to the invention is additionally preferably characterised in that tris(hydroxymethyl) aminomethane is contained in the at least one layer in an amount of from 10 to 50 wt. %, or 15 to 45 wt. %, or 15 to 40 wt. %, in relation to the total weight of the at least one layer.

The oral thin film according to the invention is additionally preferably characterised in that tris(hydroxymethyl) aminomethane is contained in the at least one layer in an amount of from 20 to 55 wt. %, or from 20 to 50 wt. %, or 20 to 45 wt. %, or 20 to 40 wt. %, in relation to the total weight of the at least one layer.

The oral thin film according to the invention is additionally preferably characterised in that tris(hydroxymethyl) aminomethane is contained in the at least one layer in an amount of from 25 to 55 wt. %, or from 25 to 50 wt. %, or 25 to 45 wt. %, or 25 to 40 wt. %, in relation to the total weight of the at least one layer.

The oral thin film according to the invention is additionally preferably characterised in that tris(hydroxymethyl) aminomethane is contained in the at least one layer in an amount of about 15 wt. %, or about 16.7 wt. %, or about 25 wt. %, or about 25.5 wt. %, or about 40 wt. %, or about 50 wt. %, in relation to the total weight of the at least one layer.

Preferably, the oral thin film according to the invention does not contain any buffer substances other than TRIS, especially no phosphates, carbonates and/or citric acid.

The oral thin film according to the invention is further preferably characterised in that no buffer substances other than TRIS, especially no phosphates, carbonates and/or citric acid, are contained in the at least one layer containing at least one polyvinyl alcohol and tris(hydroxymethyl)aminomethane (TRIS).

Preferably, no polymers other than PVA are contained in the at least one layer containing at least one polyvinyl alcohol and tris(hydroxymethyl)aminomethane (TRIS).

The oral thin film according to the invention is further preferably characterised in that the at least one layer comprises at least one pharmaceutically active agent.

Embodiments of the oral thin film according to the invention in which the oral thin film does not contain a pharmaceutically active agent, but is merely used as a "buffer thin film" are also conceivable.

The at least one pharmaceutically active agent is in principle not subject to any restrictions, but is preferably selected from all pharmaceutically active agents which are suitable for oral and/or transmucosal application.

According to the present invention, the pharmaceutically active agent also subsumes all pharmaceutically acceptable salts and solvates of the pharmaceutically active agent in question.

Preferred active agents are selected from the group comprising the active agent classes of analgesics, hormones, hypnotics, sedatives, antiepiletics, analeptics, psychoneurotropic drugs, neuro-muscle blockers, antspasmodics, antihistamines, antiallergics, cardiotonics, antiarrhythmics, diuretics, hypotensives, vasopressors, antidepressants, antitussives, expectorants, thyroid hormones, sexual hormones, antidiabetics, antitumour active agents, antibiotics, chemotherapeutics and narcotics, although this group is not exhaustive.

The at least one pharmaceutically active agent is especially preferably ketamine and/or a pharmaceutically active salt or solvate thereof, preferably ketamine HCl.

In the present case, ketamine is understood to mean (S)-(±)-2-(2-chlorophenyl)-2-(methylamino)cyclohexan-1-one, (R)-(±)-2-(2-chlorophenyl)-2-(methylamino)cyclohexan-1-one, and the racemate (RS)-(±)-2-(2-chlorophenyl)-2-(methylamino)cyclohexan-1-one.

(S)-ketamine or a pharmaceutically acceptable salt thereof, especially (S)-ketamine HCl, is especially preferably present as a single stereoisomer of ketamine, since the analgesic and anaesthetic potency of (S)-ketamine is approximately three times higher than that of the (R) form.

The active agent content in the at least one layer can vary within relatively wide limits. A content range of from 10 to 60 wt. %, in relation to the dry weight of the at least one layer, can be stated as suitable. In another embodiment, the content of active agent in the at least one layer tends to be in the range of from 25 to 35 wt. %, or in the range of from 25 to 45 wt. %, or in the range of from 25 to 55 wt. %.

The oral thin film according to the invention is further preferably characterised in that the at least one layer comprises at least one auxiliary substance selected from the group comprising colouring agents, flavourings, sweeteners, plasticisers, taste-masking agents, emulsifiers, enhancers, humectants, preservatives and/or antioxidants.

Each of these auxiliary substances is preferably contained in the at least one layer in an amount of from 0.1 to 40 wt. %, preferably from 0.1 to 30 wt. %, especially preferably from 0.1 to 15 wt. %, very especially preferably from 0.1 to 10 wt. %, or from 0.1 to 5 wt. %, in relation to the total weight of this layer.

After drying or the removal of the solvent, it is preferred that the content of residual solvent in the oral thin film is in the range of 0.2 to 15 wt. %, preferably in the range of from 0.8 to 7 wt. %, in relation to the total weight of the oral thin film.

Preferably, the oral thin film has at least one further layer comprising at least one matrix polymer and at least one pharmaceutically active agent.

In this case, the oral thin film is thus a multi-layer oral thin film.

The at least one layer comprising at least one polyvinyl alcohol and tris(hydroxymethyl)aminomethane may contain at least one pharmaceutically active agent, or, in another embodiment, may comprise no pharmaceutically active agent.

If the at least one layer containing at least one polyvinyl alcohol and tris(hydroxymethyl)aminomethane does not contain a pharmaceutically active agent, it is thus preferred that at least one of the further layers contains at least one pharmaceutically active agent.

In such a case, the at least one layer containing at least one polyvinyl alcohol and tris(hydroxymethyl)aminomethane serves only as a buffer layer that causes the adjustment of a desired pH in the patient's mouth.

The oral thin film according to the invention, which has at least one further layer comprising at least one matrix polymer and at least one pharmaceutically active agent, is preferably characterised in that the at least one polymer is a water-soluble polymer which is selected from the group comprising starch and starch derivatives, dextrans, cellulose derivatives, such as carboxymethyl cellulose, hydroxypropyl cellulose, hydroxyethyl cellulose, hydroxypropyl methylcellulose, hydroxypropyl ethyl cellulose, sodium carboxymethyl cellulose, ethyl or propyl cellulose, polyacrylic acids, polyacrylates, polyvinylpyrrolidones, vinyl pyrrolidone/vinyl acetate copolymers, polyvinyl alcohols, polyethylene oxide polymers, polyacrylamides, polyethylene glycols, gelatines, collagen, alginates, pectin, pullulan, tragacanth, chitosan, alginic acid, arabinogalactan, galactomannan, agar, agarose, carrageenan, and natural gums.

The at least one pharmaceutically active agent is in principle not subject to any restriction, but is preferably selected from all pharmaceutically active agents which are suitable for oral and/or transmucosal application.

All the active agents mentioned additionally comprise pharmaceutically acceptable salts and/or solvates thereof.

An oral thin film according to the invention, which has at least one further layer comprising at least one matrix polymer and at least one pharmaceutically active agent, is preferably characterised in that the at least pharmaceutically active agent is selected from the group comprising the active agent classes of analgesics, hormones, hypnotics, sedatives, antiepiletics, analeptics, psychoneurotropic drugs, neuromuscle blockers, antspasmodics, antihistamines, antiallergics, cardiotonics, antiarrhythmics, diuretics, hypotensives, vasopressors, antidepressants, antitussives, expectorants, thyroid hormones, sexual hormones, antidiabetics, antitumour active agents, antibiotics, chemotherapeutics and narcotics, the at least one pharmaceutically active agent preferably comprising ketamine, especially preferably (S)-ketamine.

In one embodiment, the multi-layer oral thin film according to the invention is characterised in that the at least one layer which contains at least one polyvinyl alcohol and tris(hydroxymethyl)aminomethane, and/or the at least one further layer which comprises at least one matrix polymer and at least one pharmaceutically active agent are laminated directly onto one another.

In another embodiment, the multi-layer oral thin film according to the invention is characterised in that the at least one layer which contains at least one polyvinyl alcohol and tris(hydroxymethyl)aminomethane, and/or the at least one further layer which comprises at least one matrix polymer and at least one pharmaceutically active agent or at least one flavouring are connected to one another by an intermediate adhesive layer.

An adhesive layer means a layer that can act as an adhesive as defined in DIN EN 923:2016-03. Accordingly, a non-adhesive layer cannot act as an adhesive as defined above.

Suitable adhesive coatings are, especially, water-soluble adhesive coatings as described in DE 10 2014 127 452 A1, the content of which is hereby incorporated in full.

Such adhesive layers comprise at least one water-soluble polymer and at least one plasticiser, wherein the at least one water-soluble polymer in the at least one water-soluble adhesive layer preferably comprises shellac, a vinylpyrrolidone/vinyl acetate copolymer, a polyvinylcaprolactam/polyvinyl acetate/polyethylene glycol copolymer, hydroxypropylcellulose or hydroxypropyl methylcellulose and/or polyvinylpyrrolidone, and wherein the at least one plasticiser in the at least one water-soluble adhesive layer preferably comprises glycerol, polyethylene glycol, especially polyethylene glycol 200, and/or tributyl citrate.

The weight ratio of the at least one water-soluble polymer to the at least one plasticiser in the at least one adhesive layer is preferably about 90 to 50 to about 10 to 50, preferably about 85 to 50 to about 15 to 50.

Such an adhesive layer, which contains at least one water-soluble polymer and at least one plasticiser, can, as an intermediate water-soluble adhesive layer, firmly adhere two further layers, which are not tacky per se, to one another and thus enable the construction of multi-layer oral films without multiple overcoating operations, which would mean increased drying times and increased temperature stress for the active agents and auxiliary substances contained therein.

In another embodiment, the multi-layer oral thin film according to the invention is characterised in that the at least one layer which contains at least one polyvinyl alcohol and tris(hydroxymethyl)aminomethane, and/or the at least one further layer which comprises at least one matrix polymer and at least one pharmaceutically active agent or at least one flavouring are connected to one another by an intermediate separation layer.

Preferably, a layer comprising at least one polyethylene glycol is used as the separation layer.

Polyethylene glycols (PEG) are compounds of the general formula:

$$H{+}O-CH_2-CH_2{+}_n OH$$

Higher molecular solid polyethylene glycols (melting temperature about 65 °C) are often also called polyethylene oxides or polyoxyethylenes (abbreviated to PEO or, more rarely, PEOX) or polywaxes. In this document, the terms "polyethylene glycol", "polyethylene oxide" and "polyox" are used equivalently.

The at least one polyethylene glycol preferably has a mean molecular weight of at least 20,000 g/mol to 7,000,000 g/mol, preferably from 40,000 g/mol to 500,000 g/mol, especially preferably from 95,000 g/mol to 105,000 g/mol, especially about 100,000 g/mol.

The molecular weight is derived from the rheology measurements described below.

The at least one polyethylene glycol preferably has a viscosity of 30 mPas to 50 mPas, measured at 25 °C.

The viscosities stated refer in each case to a 5 wt. % solution of polyethylene glycol in water and are measured on a Brookfield viscometer, model RVF, with spindle no. 1 at 50 rpm and at a temperature of 25 °C.

A polyethylene glycol known under the trade name POLYOX WSR N-10 (Dow Chemical) is especially preferred.

The at least one polyethylene glycol is preferably contained in the at least one separation layer in an amount of from 60 to 100 wt. %, preferably in an amount of from 80 to 100 wt. %, in relation to the total weight of the at least one separation layer.

The separation layer preferably contains at least one plasticiser, preferably glycerol, preferably in an amount of from 0.5 to 5 wt. %, especially preferably in an amount of from 2 to 2.5 wt. %, in relation to the total weight of the at least one separation layer.

One of the advantages of using such a separation layer is that polyethylene glycol films are well suited as separation layers/connection layers/adhesive layers in multi-layer oral thin films due to their smooth surface, their low melting point or glass transition temperature, their safe toxicity profile and their water solubility. When heated and/or at high pressure, polyethylene glycol adhesive layers are especially suitable for connecting two other layers to one another. For example, an active-agent-containing layer and a pH-regulating buffer layer can be connected to one another.

Furthermore, the polyethylene glycol layer is suitable as a barrier layer that prevents or minimises the migration of active agents or auxiliary substances (for example buffer salts) between the individual layers.

The separation layer also requires no or only small amounts of auxiliary substances such as plasticisers (for example 2-3% glycerol) and thus reduces the risk of migration of the adhesive layer components into the other layers of the oral thin film.

The multi-layer oral thin film according to the invention is not subject to any restrictions with regard to its structure.

Thus, embodiments are conceivable in which the multi-layer oral thin film comprises a TRIS buffer layer that does not contain a pharmaceutically active agent and another layer that contains at least one matrix polymer and at least one pharmaceutically active agent.

These two layers can be laminated directly onto one another or connected to an intermediate adhesive layer or separation layer, preferably as defined above.

Embodiments are also conceivable in which the multi-layer oral thin film consists of a TRIS buffer layer that does not contain a pharmaceutically active agent and another layer that contains at least one matrix polymer and at least one pharmaceutically active agent.

These two layers can be laminated directly onto one another or connected to an intermediate adhesive layer, preferably as defined above.

Embodiments are also conceivable in which the multi-layer oral thin film comprises a TRIS buffer layer that does not contain a pharmaceutically active agent and another layer that contains at least one matrix polymer and at least one pharmaceutically active agent, these two layers being connected by an adhesive layer or a separation layer as defined above.

Embodiments are also conceivable in which the multi-layer oral thin film consists of a TRIS buffer layer that does not contain a pharmaceutically active agent and another layer that contains at least one matrix polymer and at least one pharmaceutically active agent, these two layers being connected by an adhesive layer or a separation layer as defined above.

Other multi-layer oral thin films are conceivable, having for example the following layer structure: TRIS buffer layer—layer containing at least one matrix polymer and at least one pharmaceutically active agent,—TRIS buffer layer.

In this embodiment, the two TRIS buffer layers form outer sides of the multi-layer oral thin film.

These three layers can be either laminated directly onto one another or connected to an intermediate adhesive layer, preferably as defined above.

In principle, a modular system can be provided, more specifically with any arrangement of TRIS buffer layers and further layers.

In all the embodiments described above, the TRIS buffer layer preferably does not contain a pharmaceutically active agent. However, embodiments are also conceivable in which at least one pharmaceutically active agent is also contained in each of the TRIS buffer layers in the multi-layer thin film.

The oral thin film according to the invention is further preferably characterised in that the at least one layer which contains at least one polyvinyl alcohol and tris(hydroxymethyl)aminomethane, and/or the at least one further layer which comprises at least one matrix polymer and at least one pharmaceutically active agent is present (are present) in the form of a solidified foam having voids.

The voids and the associated larger surface area of the films facilitate especially the access of water or saliva or other bodily fluids into the interior of the dosage form and thus accelerate the dissolution of the dosage form and the release of the active agent.

In the case of a rapidly absorbing active agent, transmucosal absorption can also be improved by the rapid dissolution of the matrix layer. On the other hand, the wall thickness of said voids is preferably small, as these represent solidified bubbles, for example, so that rapid dissolution or destruction of these voids takes place.

A further advantage of this embodiment is that, despite the comparatively high area density, faster drying can be achieved by formulating as a foam than with a comparable non-foamed composition.

The oral thin film according to the invention is preferably characterised in that the voids are isolated from one another and are preferably present in the form of bubbles, the voids being filled with air or a gas, preferably with an inert gas, especially preferably with nitrogen, carbon dioxide, helium, argon or a mixture of at least two of these gases.

According to another embodiment, it is provided that the voids are connected to one another, preferably by forming a continuous channel system penetrating the matrix.

Said voids preferably have a volume fraction of from 5 to 98%, preferably from 50 to 80%, in relation to the total volume of the layer in question. In this way, the intended effect of accelerating the dissolution of the active-agent-containing matrix layer is influenced favourably.

Furthermore, surface-active agents or surfactants can be added to the matrix polymer or the polymer matrix for foam formation or to the obtained foam before or after drying in order to improve the stability of the foam before or after drying.

Another parameter that influences the properties of the dosage form according to the invention is the diameter of the voids or bubbles. The bubbles or voids are preferably created with the aid of a foam whipping machine, with which the diameter of the bubbles can be adjusted in a wide range, almost arbitrarily. Thus, the diameter of the bubbles or voids can be in the range of 1 to 350 μm. Especially preferably, the diameter is in the range of 30 and 200 μm.

The oral thin film according to the invention preferably has an area of from 0.5 $cm^2$ to about 10 $cm^2$, especially preferably from 1.5 $cm^2$ to about 9 $cm^2$.

The oral thin film according to the invention is preferably characterised in that the area density of the oral thin film is 10 to 500 $g/m^2$, preferably 100 to 400 $g/m^2$.

The area density of the TRIS buffer layer and any other layer that may be present is in each case preferably at least 10 $g/m^2$, more preferably at least 20 $g/m^2$, or at least 30 $g/m^2$, or most preferably at least 50 $g/m^2$, or less than or equal to 400 $g/m^2$, more preferably less than or equal to 350 $g/m^2$, or less than or equal to 300 $g/m^2$, or most preferably less than 250 $g/m^2$. Preferably, the area density is 10 to 400

$g/m^2$, more preferably 20 to 350 $g/m^2$, or 30 to 300 $g/m^2$, most preferably 50 to 250 $g/m^2$.

Preferably, the TRIS buffer layer and any other layer that may be present each have a layer thickness of preferably from 10 μm to 500 μm, especially preferably from 20 μm to 300 μm.

If the TRIS buffer layer is in the form of a foam, the TRIS buffer layer has a layer thickness of preferably from 10 μm to 3,000 μm, especially preferably from 90 μm to 2,000 μm.

The oral thin film according to the invention is further preferably characterised in that the oral thin film in the mouth of a patient, preferably a human, produces a pH value (at 37 °C) of from 6 to 9, preferably of from 6 to 8.

The oral thin film according to the invention is further preferably characterised in that the oral thin film produces a pH value (at 37 °C) of from 6 to 8 in 2 mL of human saliva, artificial saliva, PBS buffer or water.

The oral thin film according to the invention is further preferably characterised in that the oral thin film comprises a TRIS buffer layer and another layer containing S-ketamine HCl and produces a pH value (at 37 °C) of 6 to 8 in 2 mL of human saliva, artificial saliva, PBS buffer or water.

The oral thin film according to the invention is further preferably characterised in that the oral thin film comprises a TRIS buffer layer and another layer containing 16.3 mg of S-ketamine HCl and produces a pH value (at 37 °C) of from 6 to 8 in 2 mL of human saliva, artificial saliva, PBS buffer or water.

The oral thin film according to the invention is further preferably characterised in that the oral thin film comprises a TRIS buffer layer and another layer containing 32.2 mg of S-ketamine HCl and produces a pH value (at 37 °C) of from 6 to 8 in 2 mL of human saliva, artificial saliva, PBS buffer or water.

The present invention also relates to a kit comprising at least one first oral thin film comprising at least one layer comprising at least one polyvinyl alcohol and tris(hydroxymethyl)aminomethane, and at least one second oral thin film comprising at least one matrix polymer and at least one pharmaceutically active agent, the first and second oral thin films preferably being different. Preferably, in this kit, the first oral thin film does not comprise a pharmaceutically active agent.

The above explanations for the TRIS buffer layer and the further layer apply analogously for the first and second oral thin film which are present in the kit according to the invention.

The oral thin film according to the invention can be produced according to methods known to a person skilled in the art.

Known production methods include providing a solution comprising PVA and TRIS, then spreading and drying this solution to obtain a film.

When a multi-layer oral thin film is to be produced, a known production method includes providing a first solution comprising PVA and TRIS, then spreading and drying said solution to obtain a film, and providing a second solution comprising the at least one matrix polymer and at least one pharmaceutically active agent to obtain a second film.

The joining of these two films can be done in principle by methods known to a person skilled in the art. For example, another film can be applied to a first film by means of coating; it is irrelevant which film is coated on which film. Furthermore, the two layers can be connected to one another by an adhesive layer as described above.

The present invention further relates to an oral thin film obtainable by the method described above.

The present invention additionally relates to an oral thin film as described above, obtainable by the method or kit described above, as a medicament.

The present invention additionally relates to an oral thin film, as described above or obtainable by the method or kit described above, wherein ketamine, preferably S-ketamine (optionally as a pharmaceutically acceptable salt or ion pair), is used as pharmaceutically active agent, as a medicament for use in the treatment of pain and/or depression, especially to reduce the risk of suicide and/or for use as a general anaesthetic, preferably to initiate and carry out general anaesthesia, or as a supplement in the case of local anaesthesia and/or as an analgesic.

The present invention is explained in greater detail below in some non-limiting examples.

EXAMPLES

Example 1

Influence of pH Value on the Permeation of (S)-Ketamine HCl

Acidic Buffer:

80 g/l $Na_2HPO_4 \times 2H_2O$ dissolved in water; pH adjustment with aqueous 1M HCl solution to pH=4.99 at 22 °C.

Neutral Buffer:

80 g/l $Na_2HPO_4 \times 2H_2O$ dissolved in water; pH adjustment with aqueous 1M HCl solution to pH=7.46 at 22 °C.

Alkaline Buffer:

80 g/l $Na_2HPO_4 \times 2H_2O$ dissolved in water; pH adjustment with aqueous 1M HCl solution to pH=8.33 at 22 °C.

The pH values of this test series are summarised in Table 1.

TABLE 1

| | Buffer pH at 22° C. | Buffer pH at 37° C. | Buffer + (S)-ketamine HCl pH at 22° C. |
|---|---|---|---|
| Acidic buffer | 4.99 | 5.09 | 4.92 |
| Neutral buffer | 7.46 | 7.48 | 6.64 |
| Alkaline buffer | 8.33 | 7.91 | 7.81 |

The permeated amount of (S)-ketamine was determined by in vitro experiments according to the OECD guideline (adopted on 13 Apr. 2004) using porcine mucosa (mucosa oesophagus) and a "Franz diffusion cell". Using a dermatome, the mucosa was prepared to a thickness of 400 μm and 1.145 $cm^2$, with intact barrier function for all transmucosal therapeutic systems.

The acceptor medium was 4 mL PBS buffer with a pH value of 7.4 at 37 °C.

2.77 mg (S)-ketamine HCl were applied to the mucosa, and the mucosa with the active agent was brought into contact with the buffer solution on the upper side. The underside of the mucosa was in contact with the acceptor medium. The permeated amount of S-ketamine in the receptor medium was measured at a temperature of 37±1 °C. The results are shown in FIG. 1.

From the permeation results obtained, it can be concluded that the permeation of S-ketamine is best in neutral buffer followed by alkaline buffer. The lowest permeation rate was observed with acidic buffer.

Example 2

Influence of pH Value on the Permeation of (S)-Ketamine HCl From an Oral Thin Film.

An oral thin film of the composition according to Table 2 was prepared.

TABLE 2

| Material | Formulation 1 [wt. % ] |
|---|---|
| PVA 4-88 | 39.1 |
| TRIS | — |
| Saccharin Na | 1.0 |
| Sucralose | 2.0 |
| Cherry Flavour M55394 | 3.0 |
| Glycerol | 4.5 |
| S-ketamine HCl | 50.0 |
| FD&C Red No. 40 | 0.4 |
| Kollidon VA 64 | — |
| Solvent | Purified water |
| Area density (incl. residual moisture): | 199 g/$m^2$ |

PVA 4-88: Polyvinyl alcohol
Flavouring: MANE Cherry Flavour M55394
Colouring agent: FD&C Red No. 40

The oral thin film with the formulation according to Table 2 is produced by mass production techniques known to a person skilled in the art, for example by stirring/mixing the contained components by means of a stirring motor and suitable stirring tools.

Gas is injected into the resultant mass by stirring, for example by means of a foam whipping machine.

The foamy mass is coated onto a coating substrate in a constant layer thickness using suitable equipment (roller applicator, squeegee, coating box, etc).

All temperature-stable web-like materials from which the dry film can be removed again can serve as coating substrates. This can be ensured by the material selection of the coating substrate (different surface tensions between foamy mass and substrate), or by suitable dehesive coatings of the coating substrate with, for example, silicones or fluoropolymers.

The process solvent or solvents contained, usually water or mixtures of water and organic, water-miscible solvents, are removed by drying. The oral thin films can be provided in the appropriate size by cutting or punching from the solid foam layer thus obtained.

Acidic Buffer:

80 g/l $Na_2HPO_4 \times 2H_2O$ dissolved in water; pH adjustment with aqueous 1M HCl solution to pH=4.99 at 22 °C.

Neutral Buffer:

80 g/l $Na_2HPO_4 \times 2H_2O$ dissolved in water; pH adjustment with aqueous 1M HCl solution to pH=7.46 at 22 °C.

Alkaline Buffer:

80 g/l $Na_2HPO_4 \times 2H_2O$ dissolved in water; pH adjustment with aqueous 1M HCl solution to pH=8.33 at 22 °C.

The pH values of this test series are summarised in Table 3.

TABLE 3

| | Buffer pH at 22° C. | Buffer pH at 27° C. | Buffer + OTF pH at 22° C. | Buffer + OTF pH at 37° C. |
|---|---|---|---|---|
| Acidic buffer | 4.99 | 5.09 | 4.92 | 5.05 |
| Neutral buffer | 7.46 | 7.48 | 6.88 | 6.72 |
| Alkaline buffer | 8.33 | 7.91 | 7.91 | 7.50 |

0.287 $cm^2$ OTF (equivalent to 2.77 mg (S)-ketamine) of S-ketamine HCl formulation 1 was placed on the mucosa and 70 μL buffer solution were added.

Permeation was measured similarly to Example 1.

The permeated amount of (S)-ketamine was determined by in vitro experiments according to the OECD guideline (adopted on 13 Apr. 2004) using porcine mucosa (mucosa oesophagus) and a “Franz diffusion cell”. Using a dermatome, the mucosa was prepared to a thickness of 400 μm, with intact barrier function for all transmucosal therapeutic systems.

Punches with an area of 0.287 $cm^2$ were punched out of the OTFs, applied to the mucosa, and the mucosa with the OTFs was brought into contact on the upper side with the buffer (the underside was in contact with the acceptor medium and the upper side was cut to a mucosal area of 1.145 $cm^2$).

Figure 2:
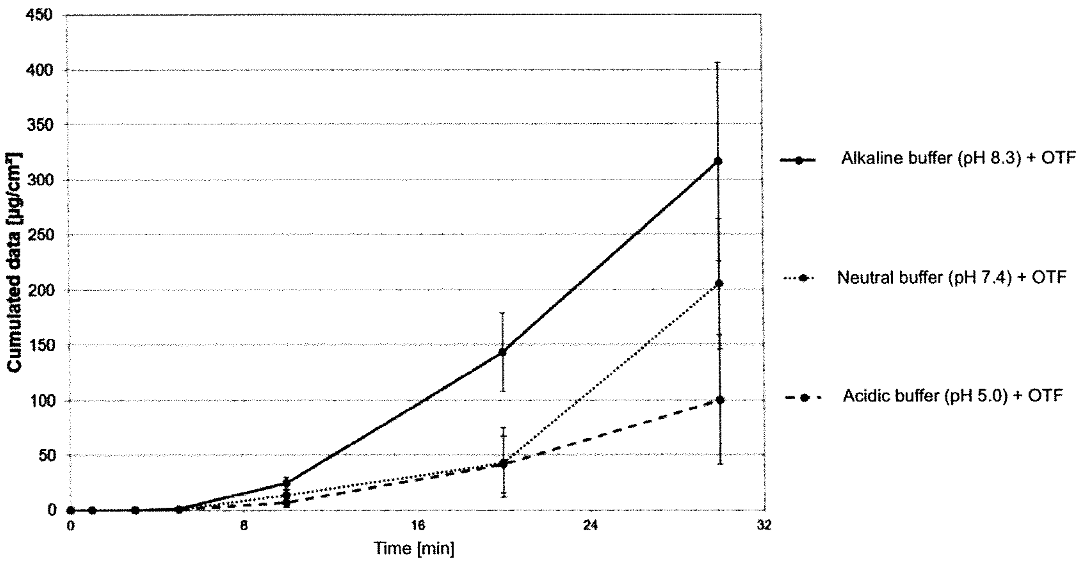

The permeated amount of S-ketamine in the receptor medium (phosphate buffer solution pH 7.4) was measured at a temperature of 37±1 °C. The results are shown in FIG. 2.

The in vitro experiments with the different buffers as donor medium showed a permeation behaviour of S-ketamine that was dependent on the pH value of the buffer used. The pH value of the donor medium including active agent is shown in Table 2 (buffer+OTF).

From the permeation results obtained, it can be concluded that the permeation of S-ketamine is best in alkaline buffer, followed by neutral buffer. The lowest permeation rate was observed with acidic buffer.

Example 3

TABLE 4

| | Formulations (amounts in wt. %) | | | | | | |
|---|---|---|---|---|---|---|---|
| Material | 2 | 3 | 4 | 5 | 6 | 7 | 8 |
| PVA 4-88 | 36.15 | 69.30 | 59.50 | 64.00 | 74.50 | 39.50 | 39.0 |
| PVA 40-88 | 36.15 | — | — | — | — | — | — |
| TRIS | 20.00 | 20.00 | 30.00 | 25.50 | 15.00 | 50.00 | 50.00 |
| Saccharin Na | 1.00 | 1.00 | 1.00 | 1.00 | 1.00 | 1.00 | 1.00 |
| Sucralose | 2.00 | 2.00 | 2.00 | 2.00 | 2.00 | 2.00 | 2.00 |
| Flavouring | — | 3.0 | 3.00 | 3.00 | 3.00 | 3.00 | 3.00 |
| Glycerol | 4.50 | 4.50 | 4.50 | 4.50 | 4.50 | 4.50 | 4.50 |
| Colouring agent | 0.20 | 0.20 | — | — | — | — | — |
| Aerosil | — | — | — | — | — | — | 0.5 |
| Process solvent: | Water | Water | Water | Water | Water | Water | Water |
| Gas for foaming | Nitrogen | Air | Air | Air | Air | Air | Air |
| pH | 3.34 $cm^2$ OTF in | — | — | 3.34 $cm^2$ OTF in | — | 3.34 $cm^2$ OTF in | — |

TABLE 4-continued

| | Formulations (amounts in wt. %) | | | | | | |
|---|---|---|---|---|---|---|---|
| Material | 2 | 3 | 4 | 5 | 6 | 7 | 8 |
| | 2 mL water pH = 9.0 (36° C.) | | | 2 mL water pH = 9.65 (21° C.) | | 2 ml water pH = 9.61 (22° C.) 3.34 $cm^2$ OTF in 2 mL glandosane pH = 9.01 (21° C.) | |

PVA 4-88: Polyvinyl alcohol
PVA 40-88: Polyvinyl alcohol
Flavouring: MANE Cherry Flavour M55394
Colouring agent: FD&C Red No. 40
Aerosil 200: Hydrophilic fumed silica with a specific surface of 200 $m^2/g$ (EVONIK)
Glandosane: artificial saliva Oral thin films with the formulations according to Table 3 were produced according to Example 2.

The oral thin films with the formulations according to Table 4 are characterised by great flexibility and a pleasant feel ("mouth feel"). Furthermore, the oral thin films produced in this way dissolve very quickly in the mouth, despite the possibly high area density and the large thickness. Due to the thin layers of the walls of the gas bubbles, very gentle drying is possible (for example 20 minutes at 70 °C for 200 $g/m^2$).

Example 4

TABLE 5

| Material | Formulation 9 [wt. %] |
|---|---|
| PVA 4-88 | 39.5 |
| TRIS | 16.7 |
| Saccharin Na | 1.0 |
| Sucralose | 2.0 |
| Flavouring | 3.0 |
| Glycerol | 4.50 |
| S-ketamine | 33.3 |
| Gas: | Air (alternatively nitrogen) |
| Process solvent | Water |
| Area density (incl. residual moisture) | 2 × 141 $g/m^2$ laminated together |
| pH | 3.34 $cm^2$ OTF in 2 mL purified water: pH = 7.5 (22° C.) pH = 7.2 (33° C.) 3.34 $cm^2$ OTF in 2 mL human saliva: pH = 7.45 (22° C.) pH = 7.28 (33.5° C.) |

PVA 4-88: Polyvinyl alcohol
Flavouring: MANE Cherry Flavour M55394

An oral thin film of the formulation according to Table 5 is produced by mass production techniques known to a person skilled in the art, for example by stirring/mixing the contained components by means of a stirring motor and suitable stirring tools.

Gas is injected into the resultant mass by stirring, for example by means of a foam whipping machine. The foamy mass is coated onto a coating substrate in a constant layer thickness using suitable equipment (roller applicator, squeegee, coating box, etc).

All temperature-stable web-like materials from which the dry film can be removed again can serve as coating substrates. This can be ensured by the material selection of the coating substrate (different surface tensions between foamy mass and substrate), or by suitable dehesive coatings of the coating substrate with, for example, silicones or fluoropolymers. The process solvent or solvents contained, usually water or mixtures of water and organic, water-miscible solvents, are removed by drying.

The two laminates were then heated to 70 °C and laminated onto each other. The oral thin films can be provided in the appropriate size by cutting or punching from the two-layer laminate thus obtained.

This two-layer oral thin film is characterised by its high layer thickness and loading. The process can be repeated as often as desired, and thus multi-layer laminates can also be obtained (for example lamination of three laminates, or four laminates), or several laminates can also be laminated together in one step (for example heat three laminates to 70 °C and laminate them together).

Example 5

TABLE 6

| | Formulation (amounts in wt. %) | | |
|---|---|---|---|
| Material | Formulation 10 | Formulation 11 | Formulation 9 |
| PVA 4-88 | 37.5 | 39.5 | 39.5 |
| TRIS | 2.0 | 25.0 | 16.7 |
| Saccharin Na | 1.0 | 1.0 | 1.0 |
| Sucralose | 2.0 | 2.0 | 2.0 |
| Flavouring | 3.0 | 3.0 | 3.0 |
| Glycerol | 4.5 | 4.5 | 4.5 |
| S-ketamine HCl | 50.0 | 25.0 | 33.3 |

TABLE 6-continued

| Material | Formulation (amounts in wt. %) Formulation 10 | Formulation 11 | Formulation 9 |
|---|---|---|---|
| Gas: | Air (alternatively nitrogen) | Air (alternatively nitrogen) | Air (alternatively nitrogen) |
| Process solvent | Water | Water | Water |
| Area density (incl. residual moisture) | 223 g/$m^2$ | 175 g/$m^2$ | 2 × 141 g/$m^2$ laminated together |
| pH | 3.34 $cm^2$ OTF in 2 mL purified water pH = 6.0 (22° C.) 3.34 $cm^2$ OTF in 2 mL glandosane pH = 5.9 (25° C.) 3.34 $cm^2$ OTF in 2 mL human saliva pH = 6.0 (25° C.) | 3.34 $cm^2$ OTF in 2 mL purified water pH = 8.26 (24° C.) 3.34 $cm^2$ OTF in 2 mL glandosane pH = 7.40 (26.5° C.) | 3.34 $cm^2$ OTF in 2 mL purified water: pH = 7.5 (22° C.) pH = 7.2 (33° C.) 3.34 $cm^2$ OTF in 2 mL human saliva: pH = 7.45 (22° C.) pH = 7.28 (33.5° C.) |

The oral thin films with the formulations according to Table 6 were produced similarly to Example 2 or Example 3.

Example 6

TABLE 7

| | Formulation 12 [wt. %] | Formulation 13 [wt. %] |
|---|---|---|
| PVA 4-88 | 39.5 | 36.15 |
| PVA 40-88 | — | 36.15 |
| (S)-ketamine HCl | 50.0 | — |
| Saccharin sodium | 1.0 | 1.0 |
| Sucralose | 2.0 | 2.0 |
| Cherry Flavour | 3.0 | — |
| Glycerol | 4.5 | 4.5 |
| TRIS | — | 20.0 |
| FD&C red 40 | — | 0.2 |
| Area density/size | 193 g/$m^2$ 3.34 $cm^2$ | 160 g/$m^2$ |
| Gas | Nitrogen | Nitrogen |
| Process solvent | Water | Water |

In each case, an oral thin film was produced according to the formulations in Table 7. The production was similar to Example 1 or Example 2.

The oral thin films were dissolved alone in water or in glandosane (artificial saliva) and the pH value of the solution was determined. Furthermore, both films were dissolved together in water or in glandosane and the pH value of the solution was determined (see Table 8).

TABLE 8

| | pH in water (2 mL) | pH in glandosane (2 mL) |
|---|---|---|
| Ketamine OTF | 5.85 | 5.11 |
| TRIS OTF | 9.65 | 8.91 |
| Ketamine OTF + TRIS OTF | 7.13 | 6.94 |

Example 7

TABLE 9

| Material | Formulation (amounts in wt. %) Formulation 1 Active agent layer | Formulation 7 Buffer layer | Formulation 14 Adhesive layer |
|---|---|---|---|
| PVA 4-88 | 39.1 | 39.5 | — |
| TRIS | — | 50.0 | — |
| Saccharin Na | 1.0 | 1.0 | — |
| Sucralose | 2.0 | 2.0 | — |
| Flavouring | 3.0 | 3.0 | |
| Glycerol | 4.5 | 4.5 | 20.0 |
| S-ketamine HCl | 50.0 | — | — |
| Colouring agent | 0.4 | — | — |
| Kollidon VA 64 | — | — | 80.0 |
| Gas | Air (alternatively nitrogen) | Air (alternatively nitrogen) | — (not foamed) |
| Process solvent | Water | Water | Ethanol |
| Area density (incl. residual moisture) | 190.0 g/$m^2$ | 2 × 113.0 g/$m^2$ | 2 × 63.1 g/$m^2$ |

PVA 4-88: Polyvinyl alcohol
Flavouring: MANE Cherry Flavour M55394
Colouring agent: FD&C Red
Kollidon VA 64: Vinylpyrrolidone-vinyl acetate copolymer Thin films were produced as active agent layer, buffer layer and adhesive layer as follows. The layers were prepared as described in Example 1 and Example 2, respectively. The composition is described in the corresponding tables.

From this, a multi-layer oral thin film with the structure buffer layer-adhesive layer-active agent layer-adhesive layer-buffer layer was produced as follows. An adhesive layer was laminated onto both sides of a ketamine laminate. After removing the carrier film, a TRIS buffer layer was then laminated onto both sides.

The result was a homogeneous foam composite with good haptic properties and a good dissolution rate for the thickness.

A pH measurement showed:

3.34 $cm^2$ OTF in 2 mL water: pH=8.07 (at 35.5 °C).

pH in 2 mL human saliva: pH=8.04 (at 36.3 °C).

Example 8

TABLE 10

| Material | Formulation (amounts in wt. %) | | |
|---|---|---|---|
| | Formulation 1 Active agent layer | Formulation 7 Buffer layer | Formulation 14 Adhesive layer |
| PVA 4-88 | 39.1 | 39.5 | — |
| TRIS | — | 50.0 | — |
| Saccharin Na | 1.0 | 1.0 | — |
| Sucralose | 2.0 | 2.0 | — |
| Flavouring | 3.0 | 3.0 | |
| Glycerol | 4.5 | 4.5 | 20.0 |
| S-ketamine HCl | 50.0 | — | — |
| Colouring agent | 0.4 | — | — |
| Kollidon VA 64 | — | — | 80.0 |
| Gas | Air (alternatively nitrogen) | Air (alternatively nitrogen) | — (not foamed) |
| Process solvent | Water | Water | Ethanol |

PVA 4-88: Polyvinyl alcohol
Flavouring: MANE Cherry Flavour M55394
Colouring agent: FD&C Red
Kollidon VA 64: Vinylpyrrolidone-vinyl acetate copolymer Thin films were produced as active agent layer, buffer layer and adhesive layer as described in Examples 1, 2 and 7, respectively. The composition is described in the corresponding tables.

From this, a multi-layer oral thin film with the structure buffer layer-adhesive layer-active agent layer was produced as follows. An adhesive layer was laminated onto a ketamine foam. After removing the carrier film of the adhesive layer, a TRIS foam was laminated on.

The result was a homogeneous foam composite with good haptic properties and a good dissolution rate for the thickness.

A pH measurement showed: 3.34 $cm^2$ OTF in 2 mL water: pH=7.97 (at 36.3 °C)

Example 9

TABLE 11

| Material | Formulation (amounts in wt. %) | | |
|---|---|---|---|
| | Formulation 1 Active agent layer | Formulation 5 Buffer layer | Formulation 14 Adhesive layer |
| PVA 4-88 | 39.1 | 64.0 | — |
| TRIS | — | 25.5 | — |
| Saccharin Na | 1.0 | 1.0 | — |
| Sucralose | 2.0 | 2.0 | — |
| Flavouring | 3.0 | 3.0 | |
| Glycerol | 4.5 | 4.5 | 20.0 |
| S-ketamine HCl | 50.0 | — | — |
| Colouring agent | 0.4 | — | — |
| Kollidon VA 64 | — | — | 80.0 |
| Gas | Air (alternatively nitrogen) | Air (alternatively nitrogen) | — (not foamed) |
| Process solvent | Water | Water | Ethanol |
| Area density (incl. residual moisture) | 187.2 $g/m^2$ | 216.9 $g/m^2$ | 78.4 $g/m^2$ |

PVA 4-88: Polyvinyl alcohol
Flavouring: MANE Cherry Flavour M55394
Colouring agent: FD&C Red
Kollidon VA 64: Vinylpyrrolidone-vinyl acetate copolymer Thin films were produced as active agent layer, buffer layer and adhesive layer as described in Examples 1, 2 and 7, respectively. The composition is described in the corresponding tables.

From this, a multi-layer oral thin film with the structure buffer layer-adhesive layer-active agent layer was produced as follows. An adhesive layer was laminated onto a ketamine foam. After removing the carrier film of the adhesive layer, a TRIS foam was laminated on.

The result was a homogeneous foam composite with good haptic properties and a good dissolution rate for the thickness.

Example 10

TABLE 12

| Material | Formulation (amounts in wt. %) | | |
|---|---|---|---|
| | Formulation 1 Active agent layer | Formulation 15 Buffer layer | Formulation 14 Adhesive layer |
| PVA 4-88 | 39.1 | 69.5 | — |
| TRIS | — | 20.0 | — |
| Saccharin Na | 1.0 | 1.0 | — |
| Sucralose | 2.0 | 2.0 | — |
| Flavouring | 3.0 | 3.0 | |
| Glycerol | 4.5 | 4.5 | 20.0 |
| S-ketamine HCl | 50.0 | — | — |
| Colouring agent | 0.4 | — | — |
| Kollidon VA 64 | — | — | 80.0 |
| Gas | not foamed | not foamed | not foamed |
| Process solvent | Water | Water | Ethanol |
| Area density (incl. residual moisture) | 187.2 $g/m^2$ | 216.9 $g/m^2$ | 78.4 $g/m^2$ |

PVA 4-88: Polyvinyl alcohol
Flavouring: MANE Cherry Flavour M55394
Colouring agent: FD&C Red
Kollidon VA 64: Vinylpyrrolidone-vinyl acetate copolymer Thin films were produced as active agent layer, buffer layer and adhesive layer as described in Examples 1, 2 and 7, respectively, although the foaming step was omitted. The composition is described in the corresponding tables.

From this, a multi-layer oral thin film with the structure buffer layer-adhesive layer-active agent layer was produced as follows. An adhesive layer was laminated onto a ketamine foam. After removing the carrier film of the adhesive layer, a TRIS foam was laminated on.

The result was a homogeneous foam composite with good haptic properties and a good dissolution rate for the thickness.

A pH measurement showed: 3.34 $cm^2$ OTF in 2 mL water: pH=6.33 (at 32 °C).

Example 11

TABLE 13

| Material | Formulation (amounts in wt. %) | | |
|---|---|---|---|
| | Formulation 12 Active agent layer | Formulation 3 Buffer layer | Formulation 16 Adhesive layer |
| PVA 4-88 | 39.5 | 69.3 | 30.0 |
| TRIS | — | 20.0 | — |
| Saccharin Na | 1.0 | 1.0 | — |
| Sucralose | 2.0 | 2.0 | — |
| Flavouring | 3.0 | 3.0 | — |
| Glycerol | 4.5 | 4.5 | 10.0 |
| S-ketamine HCl | 50.0 | — | — |
| Kollidon VA 64 | — | — | 28.0 |
| Sorbitol | — | — | 22.0 |
| Isomalt | — | — | 10.0 |

TABLE 13-continued

| | Formulation (amounts in wt. %) | | |
|---|---|---|---|
| Material | Formulation 12 Active agent layer | Formulation 3 Buffer layer | Formulation 16 Adhesive layer |
| Gas | Air (alternatively nitrogen) | Air (alternatively nitrogen) | Air (alternatively nitrogen) |
| Process solvent | Water | Water | Water |

PVA 4-88: Polyvinyl alcohol
Flavouring: MANE Cherry Flavour M55394
Colouring agent: FD&C Red Thin films were produced as active agent layer, buffer layer and adhesive layer as described in Examples 1, 2 and 7, respectively. The composition is described in the corresponding tables.

From this, a multi-layer oral thin film with the structure buffer layer-adhesive layer-active agent layer was produced as follows. An adhesive layer was laminated onto a ketamine foam. After removing the carrier film of the adhesive layer, a TRIS foam was laminated on.

The result was a homogeneous foam composite with good haptic properties and a good dissolution rate for the thickness.

Example 12

TABLE 14

| | Formulation (amounts in wt. %) | | | | |
|---|---|---|---|---|---|
| Material | 17 | 18 | 19 | 20 | 21 |
| PVA 4-88 | 39.50 | 35.2 | 57.7 | 70.2 | 63.6 |
| Caffeine | 21.83 | — | — | — | — |
| Citric acid | 10.05 | — | — | — | — |
| Sodium citrate dihydrate | 18.12 | — | — | — | — |
| Trisodium citrate | — | 54.3 | — | — | — |
| Dipotassium hydrogen phosphate | — | — | 31.8 | — | — |
| Dipotassium hydrogen phosphate | — | — | — | — | 25.9 |
| Sodium carbonate | — | — | — | 19.6 | — |
| Saccharin Na | 1.00 | 1.00 | 1.00 | 1.00 | 1.00 |
| Sucralose | 2.00 | 2.00 | 2.00 | 2.00 | 2.00 |
| Flavouring | 3.00 | 3.00 | 3.00 | 3.00 | 3.00 |
| Glycerol | 4.50 | 4.50 | 4.50 | 4.50 | 4.50 |
| Gas | Air | Mass not foamable | Mass not foamable | Mass not foamable | Mass not foamable |
| Process solvent | Water | Water | Water | Water | Water |

PVA 4-88: Polyvinyl alcohol
Flavouring: MANE Cherry Flavour M55394

The oral thin films with the formulations according to Table 14 were produced as described in Examples 1, 2 and 7.

The oral thin films with the formulations according to Table 14 showed the following disadvantages:

Lumps and inhomogeneities form in the mass. The mass is not homogeneously spreadable and thus not suitable for the production of thin films. PVA as a matrix polymer is not compatible with the salts/buffers listed in Table 14.

Example 13

TABLE 15

| | Formulation (amounts in wt. %) | | | |
|---|---|---|---|---|
| Material | 22 | 23 | 24 | 25 |
| Kollicoat Smart Seal | 34.0 | 35.0 | 41.0 | 40.0 |
| Triethyl citrate | 5.0 | — | 6.0 | 7 |
| TRIS | 50.0 | 50.0 | 40.0 | 40.0 |
| Saccharin Na | 2.0 | 1.0 | 1.0 | — |
| Sucralose | 1.0 | 2.0 | 3.0 | 3.5 |
| Flavouring | 3.0 | 3.0 | 2.0 | 2.0 |
| Glycerol | — | 7.0 | — | — |
| HPC EF | 5.0 | — | 5.5 | 5.5 |
| HPMC 90SH4000 | — | 20. | — | — |
| Cremophor RH40 | — | — | 1.5 | — |
| Polyoxy-ethylene (23) lauryl ether | — | — | — | 2.0 |
| Properties | No coatable mass | Laminate brittle; no homogeneous film | Mass not homogeneous; laminate fragile | Phase separation in the mass; not coatable |

The oral thin films with the formulations according to Table 15 were produced as described in Examples 1, 2 and 7.

The oral thin films with the formulations according to Table 15 showed the adverse properties listed in Table 15.

The aqueous polymer dispersion (Smart Seal) was provided, and plasticisers, flavourings and surfactants were added one after the other. Then, the second polymer was added. Lastly, the buffer salt was stirred in.

The mass was foamed, coated and dried according to routine methods.

Example 14

Administering formulation 2 and formulation 12 together (two separate OTFs, each 3.34 $cm^2$ OTF):

pH in 2 mL water at 36.5 °C: pH=7.15

Administering formulation 5 and formulation 12 together (two separate OTFs, each 3.34 $cm^2$ OTF):

For water:

pH in 2 mL water formulation 12 at 21 °C: pH=5.85 pH in 2 mL water formulation 5 at 21 °C: pH=9.65 pH in 2 mL water formulation 12+formulation 5 at 21 °C: pH=7.13

For glandosane (artificial saliva)

pH in 2 mL glandosane formulation 12 at 21 °C: pH=5.33 pH in 2 mL glandosane formulation 5 at 21 °C: pH=8.91 pH in 2 mL glandosane formulation 12+formulation 5 at 21 °C: pH=6.94

Administering formulation 7 and formulation 12 together (two separate OTFs, each 3.34 $cm^2$ OTF):

For water:

pH in 2 mL water formulation 12 at 21 °C: pH=5.85 pH in 2 mL water formulation 7 at 22 °C: pH=9.61 pH in 2 mL water formulation 12+formulation 7 at 22 °C: pH=7.67

For glandosane (artificial saliva)

pH in 2 mL glandosane formulation 12 at 21 °C: pH=5.33 pH in 2 mL glandosane formulation 7 at 21 °C: pH=9.01
pH in 2 mL glandosane formulation 12+formulation 7 at 21 °C: pH=7.24

Example 15

Administering formulation 13 and formulation 26 together (formulation 13 OTF 2.27 $cm^2$ OTF and 2.27 $cm^2$ formulation 26):

The composition dextromethorphan OTF: Formulation 26 is specified in Table 16.

TABLE 16

| Material | Formulation 26 [wt. % ] |
|---|---|
| Dextromethorphan | 43.78% |
| PVA 4-88 | 38.00% |
| Saccharin Na | 1.00% |
| Sucralose | 2.00% |
| Glycerol | 4.54% |
| Flavour | 6.00% |
| Amberlite IRP64 | 4.48% |
| FD&C Red 40 | 0.20% |
| Trometamol (TRIS) | — |
| Solvent | Purified water |
| Area density | 188 $g/cm^2$ |

An oral thin film with the formulation according to Table 16 were produced as described in Examples 1, 2 and 7.

A pH measurement showed: pH in 2 mL water at 35 °C: pH=7.63.

Example 16

Administering formulation 13 and formulation 27 together (formulation 13 OTF 2.27 $cm^2$ OTF and 2.27 $cm^2$ formulation 27):

The composition paracetamol (acetaminophen) OTF formulation 27 is given in Table 17.

TABLE 17

| Material | Formulation 27 [wt. %] |
|---|---|
| Paracetamol | 20.00% |
| PVA 4-88 | 72.50% |
| Saccharin Na | 0.50% |
| Sucralose | 1.00% |
| Glycerol | 4.50% |
| Flavour | 1.50% |
| Trometamol (TRIS) | — |
| Solvent | Purified water |
| Area density | 103 $g/cm^2$ |

An oral thin film with the formulation according to Table 17 were produced as described in Examples 1, 2 and 7.

A pH measurement showed: pH in 2 mL water at 33 °C: pH=8.17.

Example 18

Administering formulation 13 OTF 2.72 $cm^2$ OTF and commercial BEMA fentanyl OTF (strength 200 μg) together:

A pH measurement showed: pH in 2 mL water at 22 °C: pH=8.67.

Example 19

Determination of the influence of pH value on the permeation of protonable/deprotonable active agents. Adjustment of the pH value using a buffer OTF can reduce the variance in the pH value between individuals and bring the pH value into a preferred range for permeation. Multi-layer OTFs can influence the release profile by increasing the disintegration/dissolution time.

Ketamine OTFs with buffer substances achieve significantly better permeations (more than 18× higher) than ketamine HCl (without OTF).

Figure 3:
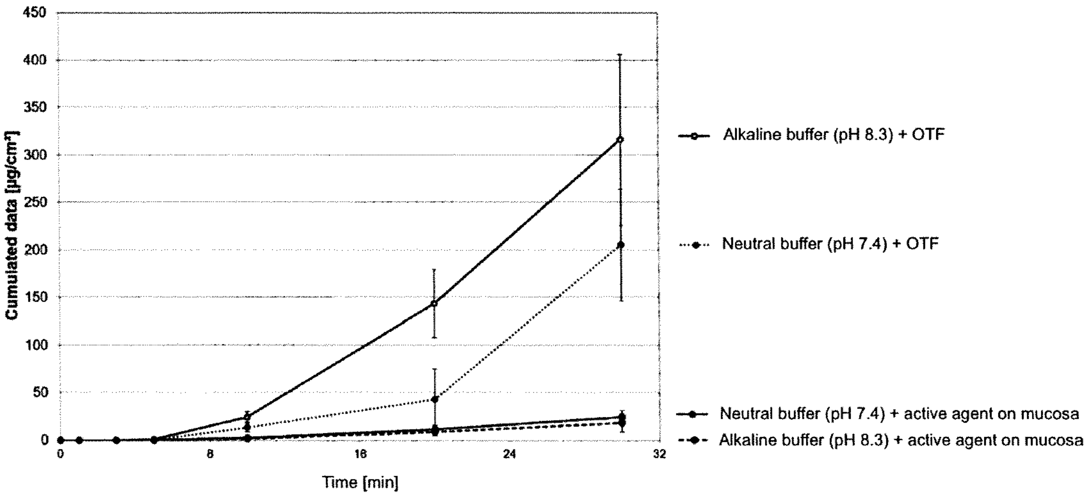

The results are summarised in FIG. 3.

The invention claimed is:

1. An oral thin film, comprising at least one layer, including polyvinyl alcohol and tris(hydroxymethyl)aminomethane, said tris(hydroxymethyl)aminomethane present in an amount from 15 to 70 wt. % in relation to the total weight of the at least one layer.

2. The oral thin film according to claim 1, characterised in that polyvinyl alcohol is contained in the at least one layer in an amount of from 20 to 90 wt. % in relation to the total weight of the at least one layer.

3. The oral thin film according to claim 1, characterised in that tris(hydroxymethyl)aminomethane is contained in the at least one layer in an amount of from 25 to 55 wt. % in relation to the total weight of the at least one layer.

4. The oral thin film according to claim 1, characterised in that the at least one layer comprises at least one pharmaceutically active agent.

5. The oral thin film according to claim 1, characterised in that the at least one layer comprises at least one pharmaceutically active agent which is selected from the group consisting of the active agent classes of analgesics, hormones, hypnotics, sedatives, antiepiletics, analeptics, psychoneurotropic drugs, neuro-muscle blockers, antspasmodics, antihistamines, antiallergics, cardiotonics, antiarrhythmics, diuretics, hypotensives, vasopressors, antidepressants, antitussives, expectorants, thyroid hormones, sexual hormones, antidiabetics, antitumour active agents, antibiotics, chemotherapeutics, narcotics and combinations thereof, the at least one pharmaceutically active agent preferably comprising ketamine, especially preferably (S)-ketamine, or pharmaceutically acceptable salts thereof.

6. The oral thin film according to claim 1, characterised in that the at least one layer comprises at least one auxiliary substance selected from the group consisting of colouring agents, flavourings, sweeteners, plasticisers, taste-masking agents, emulsifiers, enhancers, humectants, an acid or a base (or a salt thereof), preservatives and/or antioxidants.

7. The oral thin film according to claim 1, characterised in that the oral thin film has at least one further layer which comprises at least one matrix polymer and at least one pharmaceutically active agent.

8. The oral thin film according to claim 7, characterised in that the at least one polymer is a water-soluble polymer which is selected from the group consisting of starch and starch derivatives, dextrans, cellulose derivatives, such as carboxymethyl cellulose, hydroxypropyl cellulose, hydroxyethyl cellulose, hydroxypropyl methylcellulose, hydroxypropyl ethyl cellulose, sodium carboxymethyl cellulose, ethyl or propyl cellulose, polyacrylic acids, polyacrylates, polyvinylpyrrolidones, vinyl pyrrolidone/vinyl acetate copolymers, polyvinyl alcohols, polyethylene oxide polymers, polyacrylamides, polyethylene glycols, gelatines, collagen, alginates, pectin, pullulan, tragacanth, chitosan, alginic acid, arabinogalactan, galactomannan, agar, agarose, carrageenan, natural gums and combinations thereof.

9. The oral thin film according to claim 7, characterised in that the at least one pharmaceutically active agent is selected from the group consisting of the active agent classes of analgesics, hormones, hypnotics, sedatives, antiepiletics, analeptics, psychoneurotropic drugs, neuro-muscle blockers, antspasmodics, antihistamines, antiallergics, cardiotonics, antiarrhythmics, diuretics, hypotensives, vasopressors, antidepressants, antitussives, expectorants, thyroid hormones, sexual hormones, antidiabetics, antitumour active agents, antibiotics, chemotherapeutics, narcotics and combinations thereof, the at least one pharmaceutically active agent preferably comprising ketamine, especially preferably (S)-ketamine, or pharmaceutically acceptable salts thereof.

10. An oral thin film comprising at least one layer including polyvinyl alcohol and tris(hydroxymethyl)aminomethane, said tris(hydroxymethyl)aminomethane present in an amount from 15 to 70 wt. % in relation to the total weight of the at least one layer, characterised in that the oral thin film has at least one further layer which comprises at least one matrix polymer and at least one pharmaceutically active agent, and further characterised in that the at least one layer which contains at least one polyvinyl alcohol and tris(hydroxymethyl)aminomethane, and/or the at least one further layer which comprises at least one matrix polymer and at least one pharmaceutically active agent is present (are present) in the form of a solidified foam having voids.

11. The oral thin film according to claim 10, characterised in that the voids are isolated from one another and are preferably present in the form of bubbles, the voids being filled with air or a gas, preferably with an inert gas, especially preferably with nitrogen, carbon dioxide, helium or a mixture of at least two of these gases.

12. The oral thin film according to claim 10, characterised in that the voids are connected to one another and preferably form a channel system penetrating the matrix layer.

13. The oral thin film according to claim 10, characterised in that said voids account for a volume fraction of from 5 to 98%, preferably from 50 to 80%, in relation to the total volume of the layer in question.

14. The oral thin film according to claim 7, characterised in that the at least one layer which contains at least one polyvinyl alcohol and tris(hydroxymethyl)aminomethane, and/or the at least one further layer which comprises at least one matrix polymer and at least one pharmaceutically active agent are laminated directly on one another or are connected to one another by an intermediate adhesive layer or separation layer.

15. The oral thin film according to claim 1, characterised in that the oral thin film in the mouth of a patient produces a pH value (at 37 °C) of from 6 to 9.

16. The oral thin film according to claim 11, characterised in that the voids are present in the form of bubbles.

17. The oral thin film according to claim 16, characterised in that the bubbles are filled with nitrogen, carbon dioxide, helium or a mixture of at least two of these gases.

18. The oral thin film according to claim 13, characterised in that said voids account for a volume fraction from 50 to 80%, in relation to the total volume of the layer in question.

19. The oral thin film according to claim 15, characterised in that the oral thin film in the mouth of a patient produces a pH value (at 37 °C) of from 6 to 8.

20. A method of administrating a medicament comprising providing the oral thin film of claim 1 to a subject.

* * * * *